(12) United States Patent
Peng et al.

(10) Patent No.: US 8,735,601 B2
(45) Date of Patent: May 27, 2014

(54) PENTAMETHINE CYANINE FLUORESCENT DYE WITH N-SUBSTITUTING AT β-POSITION OF CONJUGATED CHAIN

(75) Inventors: Xiaojun Peng, Dalian (CN); Zhigang Yang, Dalian (CN); Fengling Song, Dalian (CN); Yanxia He, Dalian (CN); Shiguo Sun, Dalian (CN); Jiangli Fan, Dalian (CN)

(73) Assignees: Dalian University of Technology, Dalian, Liaoning (CN); Dalian Chromas Bioscience Co., Ltd., Dalian, Liaoning (CN)

( * ) Notice: Subject to any disclaimer, the term of this patent is extended or adjusted under 35 U.S.C. 154(b) by 24 days.

(21) Appl. No.: 13/521,046

(22) PCT Filed: Dec. 6, 2010

(86) PCT No.: PCT/CN2010/001971
§ 371 (c)(1),
(2), (4) Date: Jul. 7, 2012

(87) PCT Pub. No.: WO2011/085532
PCT Pub. Date: Jul. 21, 2011

(65) Prior Publication Data
US 2012/0296098 A1    Nov. 22, 2012

(30) Foreign Application Priority Data

Jan. 15, 2010   (CN) .......................... 2010 1 0010134

(51) Int. Cl.
*C07D 209/02*     (2006.01)
(52) U.S. Cl.
USPC ........................................................ 548/455

(58) Field of Classification Search
None
See application file for complete search history.

(56) References Cited

U.S. PATENT DOCUMENTS

2008/0207918 A1 *  8/2008  Aoyama et al. ............... 548/455

FOREIGN PATENT DOCUMENTS

| GB | 620801 A | | 3/1949 |
| GB | 2235463 A | * | 3/1991 |
| JP | 04-283269 A | | 10/1992 |
| JP | 2001-348500 A | | 12/2001 |

OTHER PUBLICATIONS

O. Przhonska, et al. "Investigation of excited-state relaxation processes of organic dyes by time-resolved spectroscopy" AIP Conference Proceedings (1996), 364. pp. 197-203.

* cited by examiner

*Primary Examiner* — Nyeemah A Grazier
(74) *Attorney, Agent, or Firm* — Novick, Kim & Lee, PLLC; Allen Xue (57) ABSTRACT

A pentamethine cyanine fluorescent dye with N-substituting at β-position of conjugated chain is disclosed. The dye reacts with biosubstrate including protein, liposome and DNA, and shows excellent selectivity. It has good living cell membrane permeability and shows good selectivity in living cell staining In addition, the dye has good stability and low background fluorescence, and can be used together with other fluorescent dyes having consistent wavelengths for single-channel excitation and multi-channel detection. The dye can be used in the fields of protein labeling and detecting, fluorescence immunoassay and living cell selective imaging and the like.

5 Claims, 3 Drawing Sheets

PENTAMETHINE CYANINE FLUORESCENT DYE WITH N-SUBSTITUTING AT β-POSITION OF CONJUGATED CHAIN

TECHNICAL FIELD

The present invention relates to a pentamethine cyanine fluorescent dye with N-substituting at β-position of conjugated chain which belongs to a fluorescence dye utilized in the biological fluorescence analysis technical field.

BACKGROUND ART

Fluorescent dye as a functional dye has been widely used in various fields, and attracts much attention on the research especially in life science, clinical diagnosis, fluorescent immune analysis and detection, and so on. In cell biology, fluorescence spectrum has been used in tracking of position and migration of cellular compositions. Moreover, recognition and assortment of cells also relies on the flow cytometry which is based on fluorescent technology. Therefore, the development of fluorescent dye with excellent photophysical properties is crucial to fluorescent analysis technology.

By comparison of the other fluorescent dye, cyanine fluorescent dye as a member of fluorescent dyes has prominent advantages in the application fields of ion probe, bio-labeling (DNA and protein labeling), and live cell and vivo tissue imaging, such as large molar extinction coefficient and increased maximum absorption and emission wavelengths upon elongation of conjugated chain. For example, maximum absorption and emission wavelengths of pentamethine and heptamethine cyanine dyes are above 600 nm, particularly for heptamethine cyanine dye, absorption and emission wavelengths are above 750 nm which are close to near-Infrared area, which can effectively avoid autofluorescence from bio-tissues.

Generally, Stokes shift of cyanine dye is about 20 nm, which is disadvantageous for the bioapplication of the dye. This is because small Stokes shift would cause some problems as follows:

(1) Absorption and emission spectra of the dye overlap so much that self-absorption of the dye arises. The self-absorption of the light emitted from the dye would decrease fluorescence quantum yield of the dye (generally about 0.2) and results in self-quenching.

(2) Because Stokes shift of the dye is small, maximum absorption wavelength and maximum emission wavelength of the dye are so close that scattering light of excitation light would interfere with detection results.

(3) In order to avoid the interference from the scattering light, maximum absorption wavelength cannot be adopted as excitation wavelength or detection vavelength cannot be fixed at maximum emission wavelength, which would decrease sensitivity of detection.

There are two literatures in which it was reported that small Stokes Shift of the dye would affect the detection: (1) Tolosa, L.; Nowaczyk, K.; Lakowicz, J. an Introduction to Laser Spectroscopy, 2nd ed.; Kluwer: New York, 2002. (2) Zhang Z., Achilefu S. Synthesis and Evaluation of Polyhydroxylated Near-Infrared Carbocyanine Molecular Probes. Org. Lett. 2004, 6(12): 2067-2070. To solve the above-mentioned problems, it is very meaningful to develop a fluorescent dye with excellent photophysical properties. It was reported that, when an amino group was introduced to the central position of heptamethine cyanine dye, Stokes shift of the dye could be enlarged from about 20 nm to more than 140 nm, and the fluorescence quantum yield of the dye was also enhanced. However, the longer the conjugated chain of the cyanine dye is, the worse the photostability thereof is, which restricts the further application of heptamethine cyanine dye.

Pentamethine cyanine dye is more stable than heptamethine cyanine dye, but also exists some problems for pentamethine cyanine dye in bio-application. For example:

(1) Small Stokes shift of the dye would also cause above interferences.

(2) Most of polymethine cyanine dyes are structurally symmetrical and lack of single reactive site for fluorescent labeling. In fluorescent labeling, it is better for fluorescent cyanine dye to contain a single reactive group (such as carboxyl group and the like) in the molecule for a special derivation reaction to obtain an ideal fluorescent probe molecule. In order to obtain such polymethine cyanine dye with a single carboxyl group, the usual method is to synthesize an asymmetrical cyanine dye and to intruduce a carboxyl group at one end of the molecule. However, the method makes it troublesome and difficult to synthesize and isolate the dye.

Pentamethine cyanine dye is a near-infrared cyanine dye with the shortest wavelength, and has a much better photostability than heptamethine cyanine dye. Therefore, in the present invention, a series of representative pentamethine cyanine dye with N-substituting at β-position (IIa-g) were firstly synthesized, and then their photophysical properties (spectrum and photostability) were detected, and finally non-covalent interaction of the dyes with protein was investigated.

SUMMARY OF THE INVENTION

The purpose of the present invention is to solve the problems of too small Stokes shift of pentamethine cyanine fluorescent dye, too much overlapping of absorption spectrum and emission spectrum of the dye which can result in self-absorption and self-quenching of the dye, and resultant decreased sensitivity due to scattering of excitation light and so on in bio-application of the dye, and to provide a novel pentamethine cyanine fluorescent dye with a amino group connected at β-position of the dye. According to the present invention, the increased Stokes shift of the dye, by which the problems of self-absorption and self-quenching of the dye can be solved and the bio-application effects of the dye can be enhanced, is expected.

In general structure I:

X=II;

$R_1$, $R_2$=$(CH_2)_nR_8$, $(CH_2)_mOR_9$, $(CHR_{10}CH_2O)_pR_9$ or $CH_2C_6H_4R_8$;

$R_3$, $R_4$, $R_8$=H, $SO_3R_{11}$ or $CO_2R_{12}$;

$R_5$=$(CH_2)_nR_8$, $(CH_2)_nOR_9$ or $(CHR_{10}CH_2O)_pR_9$;

$R_6$=$(CH_2)_nR_8$, $(CH_2)_mOR_9$, $(CHR_{10}CH_2O)_pR_9$, meta- or para-$C_6H_4R_{17}$;

$R_9$=H or $C_{1-18}$alkyl;

$R_{10}$=H or $CH_3$;

$R_{11}$=$N(R_{13}R_{14}R_{15}R_{16})$;

$R_{12}$=$C_{1-18}$alkyl;

$R_{13}$, $R_{14}$, $R_{15}$, $R_{16}$=H, $C_{1-18}$alkyl; $(CH_2)_mOR_9$ or $(CHR_{10}CH_2O)_pR_9$;

$R_{17}$=H, $NH_2$, $NHCOR_9$ or $(CH_2)_nR_8$; and n, m, p=0 to 18.

(1) On the basis of previous work by others, we designed a novel method to synthesize pentamethine cyanine dye, which was not reported as far as we know. A half reaction synthesis route and a witting reaction were employed to synthesize the same intermediate, and then the intermediate was utilized to synthesize a series of pentamethine cyanine dyes with amino group-substituting at deviated position of conjugated chain.

(2) In the present invention, some deviated position-substituted pentamethine cyanine dyes were synthesized. The dyes can selectively react with bio-substrate such as DNA and protein to greatly increase the fluorescence thereof. The dyes have good cell-permeability and can selectively image in live cells.

The effective results of the present invention are as follows: A dye with an amino group-substituting at β-position was synthesized, both absorption wavelength and emission wavelength of the obtained dye blue-shifted in some extent, and Stokes shift was increased to above 70 nm from about 20 nm which solved the problems of self-absorption and self-quenching of pentamethine cyanine fluorescent dye. Compared with the traditional pentamethine cyanine fluorescent dye, the synthesized dye in the present invention has largely increased fluorescence intensity upon interaction with bio-substrate. The dye of the present invention shows very good reactive selectivity with bio-substrate (protein, liposome and DNA). The dye of the present invention has live cell membrane-permeability, and shows very good selectivity in dyeing of live cells and can mainly dye liposome around nucleus of live cells.

MODE FOR CARRYING OUT THE INVENTION

EXAMPLE 1

Detailed synthesis route for intermediate was showed below.

(1)

6

Indole was synthesized by the Fisher indole synthesis method.

An amount of 54 g (0.5 mol) of phenylhydrazine was added into a 250 ml two-necked flask, and then 43 g (0.5 mol) of 3-methyl-2-butanone was added thereto dropwise under stirring. The obtained mixture was heated to 70-80° C. and reaction was carried out for 4h. The water layer was separated and the obtained water layer was extracted by diethyl ether. After combined with the diethyl ether layer, the organic phase was dried with anhydrous MgSO4. After filtration, the solvent was removed under reduced pressure. The crude hydrazone in an amount of 70 g was obtained in a yield of 80%. The obtained crude hydrazone in an amount of 70 g (0.4 mol) was mixed with 150 mL glacial acetic acid. The mixture was reacted for 4 h in an oil bath of 90° C. and then cooled down. The water layer was neutralized by an aqueous saturated Na2CO3 solution, and then water phase and organic phase were separated. The water phase was extracted by diethyl ether; the obtained extraction liquid was combined with the organic phase and then dried with anhydrous Na2SO4. After filtration, diethyl ether was removed by distillation, and then distillation under reduced pressure was carried out to collect the fraction of boiling range during 130-140° C.(0.08-0.09 Mp). The product is an oil-like liquid in an amount of 52 g (yield: 82%).

(2) Synthesis of Quaternary Ammonium Salt (1)

An amount of 3.2 g (20 mmol) of 2,3,3-trimethyl-3H-indoline and an amount of 4.7 g of iodoethane were mixed in 100 ml round bottom flask, and then about 30 ml toluene was added thereto. The mixture was refluxed for 7 h at heating condition under nitrogen protection. The liquid was cooled down to room temperature after stopping heating, and the produced solid was filtered. The obtained pink quaternary ammonium salt solid in an amount of 5.4 g was washed with diethyl ether (yield: 86%).

(3) Synthesis of Intermediate 2

1-ethyl-2,3,3-trimethyl-3H-indoline iodide quaternary ammonium salt (12.6 g, 40 mmol) was dissolved in 100 ml 20% aqueous NaOH solution, and the mixture was stirred for 1 h at room temperature. The reaction mixture was extracted with anhydrous diethyl ether (3×50 ml), and then dried with anhydrous $Na_2SO_4$. Diethyl ether was removed under reduced pressure to give a 7 g yellow oil-like liquid in a yield of 94%. Because the oil-like liquid would turn to red color by exposure to air for a long time, the subsequent reaction was carried out immediately.

(4) Synthesis of Intermediate 3

In an ice bath, $POCl_3$ (4.7 g, 30 mmol) was added dropwise during a period of 30 minutes to 20 ml freshly-distilled DMF, and then stirred for 30 minutes. 1 (4.5 g, 25 mmol) dissolved in 15 ml DMF was added dropwise thereto and heated at 90° C. for 2 h. After being cooled down, the reaction solution was poured into 200 ml ice-water mixture, neutralized with $Na_2CO_3$, extracted with $CH_2Cl_2$ (3×50 ml) and dried with anhydrous $Na_2SO_4$. The solvent was removed by rotatory evaporation, and then purification was carried out with silica gel column chromatography (petroleum ether/$CH_2Cl_2$=1:1 (v/v)) to give a 4 g yellow solid in a yield of 74%.

$^1$H-NMR (400 MHz, $CDCl_3$)1.27 (t, 3H, $CH_3$, J=6.8 Hz), 1.66 (s, 6H, $CH_3$), 3.748 (q, 2H, $CH_2$, J=6.8 Hz), 5.42 (d, 1H, CH, J=9.2 Hz), 6.85 (d, 1H, ArH, J=7.6 Hz), 7.06 (t, 1H, ArH, J=7.6 Hz), 7.27 (t. 1H, ArH, J=7.6 Hz), 7.28 (d, 1H, ArH, J=7.6 Hz), 10.02 (d, 1H, CHO, J=9.2 Hz);

$^{13}$C-NMR (100 MHz, $CDCl_3$): 11.21, 29.69, 37.71, 47.66, 98.64, 108.10, 122.03, 122.55, 128.19, 139.74, 142.66, 172.72, 186.75;

HRMS: m/z calcd $M^+$ for $C_{14}H_{17}NO$ 215.1310; found, 215.1314.

(5) Synthesis of Intermediate 4

This compound was synthesized according to the reported method except that $CH_2Cl_2$ was used as the solvent instead of the toxic benzene. The details were showed below. 1 (7 g, 37.4 mmol) and triethylamine (4.9 g, 48.6 mmol) were mixed in 100 ml anhydrous $CH_2Cl_2$. In an ice bath, chloroacetyl chloride (5.03 g, 44.9 mmol) dissolved in about 20 ml $CH_2Cl_2$ was added dropwise thereto during a period of 0.5 h. After that, the ice bath was removed and the reaction was continuously carried out at room temperature for 2 h. The reaction solution was washed with water, extracted with $CH_2Cl_2$ (3×50 ml) and dried with anhydrous $Na_2SO_4$. The solvent was removed under reduced pressure, and then purification was carried out with silica gel column chromatography (eluting solvent: petroleum ether/$CH_2Cl_2$=2:1 (v/v)) to give a light yellow oil-like liquid which slowly changed into a solid in an amount of 6.8 g in a yield of 74%.

$^1$H-NMR (400 MHz, $CDCl_3$): 1.28 (t, 3H, $CH_3$, J=7.2 Hz); 1.72 (s, 6H, $CH_3$); 3.80 (q, 2H, $CH_2$); 4.09 (s, 2H, $CH_2$), 5.57 (s, 1H, CH), 6.81 (1H, ArH, J=7.6 Hz), 7.03 (t, 1H, ArH, J=7.6 Hz), 7.20 (t, 1H, ArH, J=7.6 Hz), 7.22 (d, 1H, ArH, J=7.6 Hz);

$^{13}$C-NMR (100 MHz, $CDCl_3$): 11.07, 22.66, 22.81, 37.68, 48.71, 48.59, 88.43, 108.07, 121.96, 122.78, 127.60, 140.23, 142.32, 172.40, 186.33;

HRMS: m/z calcd M+ for $C_{15}H_{18}NOCl$, 263.1077; found, 271.1085.

(6) Synthesis of Intermediate 5

4 (6.8 g, 26.2 mmol) and triphenylphosphine (10 g, 40 mmol) were dissolved in 100 ml toluene, and the mixture was refluxed for 10 h at heating condition under nitrogen protection. After being cooled down to room temperature, the solid product was filtered and washed with anhydrous diethyl ether to give a milky white solid quaternary phosphonium salt in an amount of 10.5 g in a yield of 76.5%. Because it may be destroyed by moisture, the quaternary phosphonium salt was used directly for the next reaction without further treatment.

(7) Synthesis of Intermediate 5

3 (10.5 g, 20 mmol) and 4 (4.3 g, 20 mmol) were added in a mixed solvent of 50 ml anhydrous methanol and 25 ml anhydrous THF. In an ice bath, NaH (1.0 g) was added in batch thereto during a period of 1 h and the reaction was continuously carried out for 2 h. Then the ice bath was removed and the solution was stirred for 24 h at room temperature. The solvent was removed under reduced pressure, and the obtained residue was washed with water, extracted with $CH_2Cl_2$ and dried with anhydrous $Na_2SO_4$. Then, the solvent was removed by rotation evaporation and purification was carried out with silica gel chromatography (petroleum ether/$CH_2Cl_2$=2:1 (v/v)) to give a light yellow oil-like liquid which slowly changed into a yellow solid in an amount of 4.0 g in a yield of 47%.

EXAMPLE 2

Synthesis of Aimed Dye (8) Synthesis of Dye IIa 5 (0.425 g, 1 mmol) was dissolved in 10 ml anhydrous THF, and $POCl_3$ (0.616 g, 4 mmol) was added thereto, then the solution was heated to reflux for 1 h under nitrogen protection until the solution turned into blue color from yellow color. The solution was cooled down to room temperature to obtain a THF solution of intermediate 6. Because 6 is very active, it was used directly for the next further treatment without being separated. After the solvent was removed under reduced pressure, 10 ml THF was added, and then a THF solution of ammonia was added under stirring until the obtained solution turned to orange color from blue color. The solvent was removed under reduced pressure. The residue was washed with water, extracted with $CH_2Cl_2$ and dried with anhydrous $Na_2SO_4$, and the solvent was removed under reduced pressure. Purification was carried out with silica gel column chromatography ($CH_2Cl_2$/methanol 50:1 (v/v)) to give a red solid in an amount of 0.08 g in a yield of 17%.

$^1$H-NMR (400 MHz, $CDCl_3$):1.19 (t, 3H, $CH_3$, J=7 Hz); 1.30 (t, 3H, $CH_3$, J=7 Hz); 1.51 (s, 6H, $CH_3$) , 1.54(s, 6H, $CH_3$); 2.24(2H, $NH_2$); 3.80(q, 2H, $CH_2$, J=6.8 Hz); 3.92(q, 2H, $CH_2$, J=6.4 Hz); 5.34(s, 1H, CH); 5.75(d, 1H, CH, J=12.8 Hz); 6.51(d, 1H, CH, J=14 Hz); 6.84(t, 2H, ArH, J=6.4 Hz); 7.01(t, 1H, ArH, J=7.2 Hz); 7.05(d, 1H, ArH, J=7.8 Hz); 7.16(d, 1H, ArH, J=7.2 Hz); 7.23-7.28(4H, ArH); 8.00(t, 1H, CH, J=12.8 Hz);

$^{13}$C-NMR (100 MHz, $CDCl_3$): 11.56, 11.64, 28.50, 28.65, 37.73, 47.50, 48.18, 53.45, 96.58, 108.05, 109.18, 114.24, 121.92, 122.20, 122.44, 122.53, 128.08, 128.13, 138.75, 140.03, 142.61, 146.76, 167.22, 168.90;

HRMS: m/z calcd $M^+$ for $C_{29}H_{36}N_3^+$, 426.2909; found, 426.2901.

EXAMPLE 3

(9) Synthesis of Dye IIb 5 (0.425 g, 1 mmol) was dissolved in 10 ml anhydrous THF, and $POCl_3$ (0.616 g, 4 mmol) was added thereto, then the solution was heated to reflux for 1 h under nitrogen protection until the solution turned into blue color from yellow color. The solution was cooled down to room temperature to obtain a THF solution of intermediate 6. After the solvent was removed under reduced pressure, 10 ml THF was added, and then a THF solution of ethanol amine (0.92 g, 15 mmol) was added under stirring until the obtained solution turned to orange color from blue color. The solvent was removed under reduced pressure. The residue was washed with water, extracted with $CH_2Cl_2$ and dried with anhydrous $Na_2SO_4$, and the solvent was removed under reduced pressure. Purification was carried out with silica gel column chromatography ($CH_2Cl_2$/methanol 50:1 (v/v)) to give a red solid in an amount of 0.15 g in a yield of 36%.

$^1$H-NMR (400 MHz, $CDCl_3$): 1.07 (t, 3H, $CH_3$, J=6.8 Hz), 1.30 (s, 6H, $CH_3$), 1.34 (3H, $CH_3$, J=6.8 Hz), 1.52 (s, 6H, $CH_3$), 3.47 (t, 2H, $CH_2$), 3.72 (q, 2H, CH2, J=6.8 Hz) 3.80 (q, 2H, $CH_2$, J=6.8 Hz), 4.01 (t, 2H, $CH_2$, J=6.8 Hz), 4.87 (s, 1H, CH), 5.79 (d, 1H, CH, J=13.2 Hz), 6.77 (t, 1H, ArH, J=8 Hz), 6.74 (d, 1H, CH, J=13.2 Hz), 6.83 (d,1H, ArH, J=8 Hz), 6.70 (t, 1H, ArH, J=8 Hz), 7.04 (t, 1H, ArH, J=7.2 Hz), 7.10 (d, 1H, ArH, J=7.2 Hz), 7.23 (d, 1H, ArH, J=7.2 Hz), 7.25 (t, 1H, ArH, J=8 Hz), 7.27 (d, 1H, ArH, J=8 Hz), 7.78 (t, 1H, CH, J=13.2 Hz), 11.09 (s, 1H, NH);

$^{13}$C-NMR (100 MHz, CDCl$_3$): 11.55, 11.79, 29.47, 29.64, 29.80, 30.68, 37.92, 39.98, 47.32, 47.94, 50.32, 59.20, 81.22, 96.81, 108.29, 108.92, 114.58, 121.87, 122.14, 122.41, 122.51, 128.33, 128.95, 137.79, 139.78, 142.73, 144.51, 148.02, 167.17, 167.82, 171.31;

HRMS: m/z calcd M$^+$ for C$_{31}$H$_{40}$N$_3$O$^+$ 470.3166; found, 470.3162.

EXAMPLE 4

(10) Synthesis of Dye IIc

The synthesis method thereof is similar to that of IIb. Yield: 35%.

$^1$H-NMR and $^1$H-$^1$H NMR (400 MHz, Acetone-d$_6$): 1.09 (t, 3H, CH$_3$, J=6.4 Hz), 1.29 (t, 3H, CH$_3$, J=6.4 Hz); 1.29 (s, 6H, CH$_3$); 1.60 (s, 6H, CH$_3$); 3.84-3.96 (m, 8H, CH$_2$); 4.05 (t, 4H, CH$_2$, J=6.4 Hz), 5.58 (s, 1H, CH), 5.95 (d, 1H CH, J=11.2 Hz), 6.56 (d, 1H, CH, J=12.4 Hz), 6.88 (d, 1H, ArH, J=8 Hz), 6.97 (t, 1H, ArH, J=7.8 Hz), 7.03 (t, 1H, ArH, J=7.8 Hz), 7.13 (d, 1H, ArH, J=8 Hz), 7.18 (t, 1H, ArH, J=7.2 Hz), 7.27 (d, 1H, ArH, J=7.8 Hz), 7.30 (t, 1H, ArH, J=7.8 Hz), 7.37 (d, 1H, ArH, J=7.2 Hz), 7.91 (t, 1H, CH, J=11.2 Hz);

$^{13}$C-NMR (100 MHz, Acetone-d$_6$): 12.24, 12.43, 14.35, 23.33, 28.76, 32.63, 38.73, 40.59, 48.37, 54.76, 54.99, 57.43, 59.57, 59.97, 85.17, 99.68, 109.32, 109.96, 113.19, 122.13, 122.80, 123.07, 123.77, 128.82, 129.12, 138.7, 141.14, 143.39, 145.94, 152.96, 165.51, 169.77, 171.61;

HRMS: m/z calcd M$^+$ for C$_{33}$H$_{44}$N$_3$O$_2^+$ 514.3434; found, 514.3449.

EXAMPLE 5

(11) Synthesis of Dye IId

The synthesis method thereof is similar to that of IIb. Yield: 31%.

$^1$H-NMR (400 MHz, CDCl$_3$): 0.86(t, 3H, CH$_3$, J=6.4 Hz); 1.05(t, 3H, CH$_3$, J=6.4 Hz); 1.26(s, 6H, CH$_3$); 1.37(s, 6H, CH$_3$); 1.47(t, 3H, CH$_3$); 1.54(t, 3H, CH$_3$); 3.71(4H, CH$_2$); 3.85(2H, CH$_2$); 4.04(q, 2H, CH$_2$); 4.80(s, 1H, CH); 6.41(d, 1H, CH, J=13.2 Hz); 6.67(d,1H, CH, J=12.4 Hz); 6.72(d, 1H, ArH, J=7.6 Hz); 6.95(d, 1H, ArH, J=8 Hz); 7.00(t, 1H, ArH, J=7.6 Hz), 7.05(t, 1H, ArH, J=7.6 Hz); 7.11(d, 1H, ArH, J=6.8 Hz); 7.19(t, 1H, ArH, J=7.6 Hz); 7.25(d, 1H, ArH, J=7.6 Hz); 7.29(t, 1H, ArH, J=7.6 Hz); 7.85(t, 1H, CH, J=12.4 Hz);

$^{13}$C-NMR (100 MHz, CDCl$_3$): 11.85, 12.18, 12.87, 13.45, 14.55, 22.89, 28.76, 31.63, 38.03, 39.99, 49.27, 55.16, 55.99, 59.91, 85.07, 98.99, 109.10, 109.97, 112.59, 122.25, 122.65, 123.47, 123.77, 128.93, 129.65, 138.67, 141.84, 143.99, 145.71, 152.69, 165.53, 169.72, 171.66;

HRMS: m/z calcd M$^+$ for C$_{33}$H$_{44}$N$_3^+$ 482.3530; found, 482.0822.

EXAMPLE 6

(12) Synthesis of Dye IIe

The synthesis method thereof is similar to that of IIb. Yield: 29%.

$^1$H-NMR (400 MHz, CDCl$_3$):0.90(t, 3H, CH$_3$, J=6.4 Hz); 1.28(t, 3H, CH$_3$, J=6.4 Hz); 1.29(s, 6H, CH$_3$); 1.44(s, 6H, CH$_3$); 3.65(q, 2H, CH$_2$, J=6.4 Hz); 3.79(q, 2H, CH$_2$, J=6.4 Hz); 4.71(s, 2H, CH$_2$); 4.72(s, 1H, CH); 5.81(d, 1H, CH, J=13.2 Hz); 6.70(d, 1H, CH, J=7.6 Hz); 6.83(d, 1H, ArH, J=8 Hz); 6.96-7.07(4H, ArH); 7.18-7.25(4H, ArH); 7.32(t, 2H, ArH, J=7.6 Hz); 7.47(d, 2H, ArH, J=7.2 Hz); 7.76(t, 1H, CH, J=12.8 Hz); 12.2(s, 1H, NH);

$^{13}$C-NMR (100 MHz, CDCl$_3$): 11.81, 12.31, 28.23, 29.76, 39.53, 40.12, 54.51, 82.97, 100.35, 108.92, 109.52, 110.85, 122.06, 122.55, 124.46, 126.57, 127.15, 128.59, 128.71, 129.63, 134.69, 137.40, 140.52, 141.96, 168.39, 172.09;

HRMS: m/z calcd M$^+$ for C$_{36}$H$_{42}$N$_3^+$, 516.3373; found, 516.3381.

EXAMPLE 7

(13) Synthesis of Dye IIf

The synthesis method thereof is similar to that of IIb. Yield: 29%.

$^1$H-NMR (400 MHz, CDCl$_3$): 1.09 (t, 3H, CH$_3$, J=6.8 Hz), 1.26 (s, 6H, CH$_3$),1.37 (t, 3H, CH$_3$, J=6.8 Hz), 1.47 (s, CH$_3$, 6H), 4.06 (q, 4H, CH$_2$, J=6.8 Hz), 4.92 (s, 4H, CH$_2$), 5.12 (s, 1H, CH), 6.33 (d, 1H, CH, J=12.8 Hz), 6.65 (d, 1H, CH, J=12.8 Hz), 6.76 (d, 1H, ArH, J=8 Hz), 7.01 (t, 2H, ArH J=7.2 Hz), 7.10 (q, 2H, ArH, J=8 Hz), 7.21 (q, 4H, ArH, J=7.6 Hz), 7.31 (m, 4H, ArH), 7.38 (t, 2H, ArH, J=7.2 Hz), 7.44 (t, 2H, ArH, J=7.2 Hz), 7.89 (t, 1H, CH, J=12.8 Hz);

$^{13}$C-NMR (100 MHz, CDCl$_3$): 11.84, 12.41, 28.48, 29.58, 39.23, 39.73, 54.60, 83.07, 100.28, 108.83, 109.32, 110.18, 121.99, 122.45, 124.43, 126.75, 127.35, 128.56, 128.77, 129.62, 134.63, 137.42, 140.55, 141.95, 168.48, 171.81;

HRMS: m/z calcd M$^+$ for C$_{43}$H$_{48}$N$_3^+$606.3843; found, 606.3832.

EXAMPLE 8

(14) Synthesis of Dye IIg

The synthesis method thereof is similar to that of IIb. Yield: 32%.

$^1$H-NMR (400 MHz, CDCl$_3$): 1.20 (t, 3H, CH$_3$, J=6.8 Hz), 1.26 (s, 6H, CH$_3$), 1.32 (t, 3H, CH$_3$, J=6.8 Hz), 1.47 (s, 6H, CH$_3$), 3.87 (q, 4H, CH$_2$, J=6.8 Hz), 4.79 (s, 1H, CH), 5.08 (d, 1H, CH, J=12.4 Hz), 6.04 (d, 1H, CH, J=12.4 Hz), 6.77 (d, 1H, ArH, J=7.6 Hz), 6.87 (d, 1H, ArH, J=8 Hz), 7.03 (q, 2H, ArH, J=6.4 Hz), 7.10 (d, 1H, ArH, J=7.2 Hz), 7.16 (d, 1H, ArH, J=7.2 Hz), 7.20 (t, 1H, ArH, J=8 Hz), 7.25 (d, 2H, ArH, J=8 Hz), 7.32 (t, 2H, ArH, J=7.6 Hz), 7.62 (d, 2H, ArH, J=8.0 Hz), 7.85 (t, 1H, CH, J=12.4 Hz);

$^{13}$C-NMR (100 MHz, CDCl$_3$): 11.89, 11.99, 28.66, 29.12, 29.69, 38.14, 40.31, 47.61, 48.19, 85.54, 98.32, 108.67, 108.87, 121.85, 122.22, 122.32, 122.98, 123.57, 126.41, 128.17, 128.32, 128.98, 138.68, 140.07, 142.37, 144.31, 148.85, 165.48, 168.27;

HRMS: m/z calcd M$^+$ for C$_{35}$H$_{40}$N$_3^+$ 502.3217; found, 502.3241.

EXAMPLE 9

The solutions of compounds IIa to IIc in a concentration of 1×10$^{-6}$M (10 mM PBS buffer (pH=7.4) was used as solvent)

was prepared, and 3 ml of the each dye solution was added into a cuvette, respectively. Then, an aqueous bovine serum albumin (BSA) stock solution with the concentration of 50 µg/µL (750 µM) was added dropwise into each of the dye solution. The fluorescence intensity of the dye was measured each 5 minutes after addition of BSA for fluorescence becoming stable, on UV-visible spectrophotometer (Mode: Hp8453) and fluorescence spectrophotometer (Mode: FP-6500).

EXAMPLE 10

The solutions of compounds IIa to IIc in a concentration of $1\times10^{-6}$ M (10 mM PBS buffer (pH=7.4) was used as solvent) was prepared, and 3 ml of the each dye solution was added into a cuvette separately. Then, an aqueous calf thymus DNA stock solution was prepared, the concentration of the calf thymus DNA stock solution was determined as $1.5\times10^{-3}$ mM by the absorbance at 260 nm on UV absorption spectrophotometer. The calf thymus DNA stock solution was added dropwise into each of the dye solution. The fluorescence intensity of the dye was measured each 5 minutes after addition of BSA for fluorescence becoming stable, on UV-visible spectrophotometer (Mode: Hp8453) and fluorescence spectrophotometer (Mode: FP-6500).

EXAMPLE 11

Observation of dying of compound A to live MCF-7 cells under laser confocal scan microscope:

Compound IIc and traditional Cy5 (5 µM) in PBS buffer (12 µl) were added into a six-well plate on which MCF-7 cells were cultured, and then incubation was performed at 37° C. for 30 minutes in an incubator with 5% $CO_2$ atmosphere. Then the plate was rinsed with fresh PBS buffer (5 ml×3) under shaking condition, and culture medium was added. The cells were observed under laser confocal scan microscope (TCS-SP2, Germany) to select representative area. Traditional Cy5 was excited at 633 nm and dye IIc was excited at 543 nm, and observation was carried out under oil immersion lens (1000×) for 3 times.

TABLE 1

Spectral properties of dyes IIa to IIg in different solvents

| Dyes | Solvents | $\lambda_{abs1}$ | $\lambda_{bs2}$ | $\lambda_{em}$ | $\Delta\lambda_1$ | $\Delta\lambda_2$ | $\epsilon_1{}^a$ | $\epsilon_2{}^a$ | $\Phi_1{}^b$ | $\Phi_2{}^b$ |
|---|---|---|---|---|---|---|---|---|---|---|
| IIa | DCM | 546 | 418 | 609 | 63 | 191 | 5.4 | 1.6 | 0.115 | 0.032 |
|  | THF | 526 | 408 | 590 | 64 | 182 | 4.8 | 1.6 | 0.053 | 0.008 |
|  | Ethanol | 527 | 420 | 602 | 75 | 182 | 4.8 | 2.0 | 0.014 | 0.009 |
|  | Methanol | 528 | 418 | 606 | 78 | 188 | 5.1 | 2.0 | 0.007 | 0.004 |
|  | DMSO | 533 | 419 | 608 | 75 | 189 | 4.9 | 1.7 | 0.020 | 0.009 |
|  | Water | 527 | 416 | 619 | 92 | 203 | 3.6 | 1.7 | 0.002 | 0.001 |
| IIb | DCM | 517 | 429 | 596 | 79 | 167 | 3.4 | 1.7 | 0.014 | 0.100 |
|  | THF | 503 | 427 | 585 | 82 | 158 | 3.6 | 2.2 | 0.085 | 0.075 |
|  | Ethanol | 521 | 435 | 612 | 91 | 177 | 3.3 | 2.3 | 0.019 | 0.017 |
|  | Methanol | 519 | 433 | 608 | 89 | 175 | 3.1 | 2.4 | 0.009 | 0.008 |
|  | DMSO | 515 | 436 | 606 | 91 | 170 | 3.0 | 2.3 | 0.009 | 0.008 |
|  | Water | 517 | 430 | 620 | 103 | 190 | 2.1 | 1.7 | 0.002 | 0.002 |
| IIc | DCM | 526 | 454 | 622 | 96 | 168 | 2.8 | 2.1 | 0.124 | 0.061 |
|  | THF | 517 | 450 | 605 | 88 | 155 | 3.1 | 1.9 | 0.109 | 0.099 |
|  | Ethanol | 521 | 451 | 618 | 97 | 167 | 2.8 | 2.3 | 0.014 | 0.013 |
|  | Methanol | 522 | 450 | 619 | 97 | 169 | 3.1 | 2.2 | 0.007 | 0.008 |
|  | DMSO | 515 | 458 | 612 | 97 | 154 | 2.5 | 2.1 | 0.005 | 0.005 |
|  | Water | 517 | 447 | 615 | 98 | 168 | 1.8 | 1.9 | 0.001 | 0.001 |
| IId | DCM | 523 | 453 | 611 | 88 | 158 | 4.3 | 2.9 | 0.124 | 0.085 |
|  | THF | 517 | 450 | 604 | 87 | 154 | 4.1 | 2.1 | 0.030 | 0.022 |
|  | Ethanol | 516 | 453 | 610 | 94 | 157 | 3.5 | 2.5 | 0.009 | 0.009 |
|  | Methanol | 513 | 451 | 609 | 96 | 158 | 3.9 | 2.8 | 0.005 | 0.005 |
|  | DMSO | 508 | 460 | 600 | 92 | 140 | 3.9 | 2.7 | 0.004 | 0.004 |
|  | Water | 501 | 448 | 600 | 99 | 152 | 2.9 | 2.3 | 0.001 | 0.001 |
| IIe | DCM | 522 | 418 | 603 | 81 | 185 | 2.8 | 2.1 | 0.106 | 0.075 |
|  | THF | 510 | 426 | 596 | 86 | 170 | 2.9 | 2.2 | 0.085 | 0.075 |
|  | Ethanol | 519 | 429 | 608 | 89 | 179 | 2.8 | 2.3 | 0.019 | 0.017 |
|  | Methanol | 517 | 431 | 605 | 88 | 174 | 2.7 | 2.2 | 0.008 | 0.007 |
|  | DMSO | 515 | 433 | 607 | 92 | 174 | 2.6 | 2.3 | 0.009 | 0.008 |
|  | Water | 516 | 429 | 617 | 101 | 188 | 2.3 | 1.9 | 0.003 | 0.001 |
| IIf | DCM | 528 | 453 | 615 | 87 | 162 | 3.1 | 2.1 | 0.113 | 0.105 |
|  | THF | 523 | 453 | 609 | 86 | 156 | 4.0 | 2.0 | 0.036 | 0.034 |
|  | Ethanol | 528 | 452 | 615 | 87 | 163 | 3.4 | 2.5 | 0.010 | 0.009 |
|  | Methanol | 527 | 451 | 617 | 90 | 166 | 3.4 | 2.5 | 0.005 | 0.004 |
|  | DMSO | 521 | 460 | 611 | 90 | 151 | 3.3 | 2.2 | 0.004 | 0.005 |
|  | Water | 525 | 447 | 618 | 93 | 171 | 2.5 | 1.9 | 0.001 | 0.002 |
| IIg | DCM | 570 | 465 | 645 | 75 | 180 | 3.6 | 2.1 | 0.064 | 0.055 |
|  | THF | 556 | 403 | 639 | 83 | 236 | 0.9 | 2.8 | 0.037 | 0.0002 |
|  | Ethanol | 563 | 434 | 640 | 77 | 206 | 2.5 | 2.0 | 0.019 | 0.006 |
|  | Methanol | 561 | 430 | 638 | 77 | 208 | 2.3 | 2.2 | 0.011 | 0.004 |
|  | DMSO | 566 | 416 | 646 | 80 | 230 | 1.9 | 2.1 | 0.014 | 0.002 |
|  | Water | 559 | 440 | 640 | 81 | 200 | 1.7 | 2.2 | 0.003 | 0.001 |

[a] Unit of molar extinction coefficient is $cm^{-1}M$.
[b] Measurement of fluorescence quantum yield; absorption and emission spectra of dyes in different solvents. Rhodanmine B in ethanol solution ($\Phi_f$ = 0.97) was used as reference. UV-visible spectrophotometer (Mode: Hp8453) and fluorescence spectrophotometer (Mode: FP-6500) were used.

1. Synthesis of Dyes

The starting material para-substituted phenylhydrazine was refluxed with 3-methyl-2-butanone in glacial acetic acid to obtain a water insoluble indole intermediate, and then the indole intermediate was quaternized by an alkylation reagent under nitrogen protection to obtain an alkyl-substituted indole intermediate quaternery ammonium salt. The obtained quaternary ammonium salt was used as a starting material for the next synthesis reaction and two synthesis routes were earthed out. Firstly, the quaternery ammonium salt was stirred in alkaline solution at ambient temperature to obtain a fischer base and then to obtain intermediate with aldehyde group in $DMF/POCl_3$. In another aspect, the fischer base was reacted with chloroacetyl chloride with triethylamine as base, and the obtained intermediate was refluxed with triphenylphosphine to obtain a witting reagent. The two intermediates were reacted in anhydrous methanol and anhydrous THF under stirring at ambient temperature to obtain intermediate with deviated position-carbonyl group. The obtained intermediate was reacted with $POCl_3$ to give an intermediate dye with chloro-group at deviated position, and then the obtained intermediate dye was reacted with different amines at ambient temperature to give the corresponding pentamethine cyanine fluorescent dye with amino group-substituting at deviated position.

2. Spectral Properties of Dyes

Figure 1:
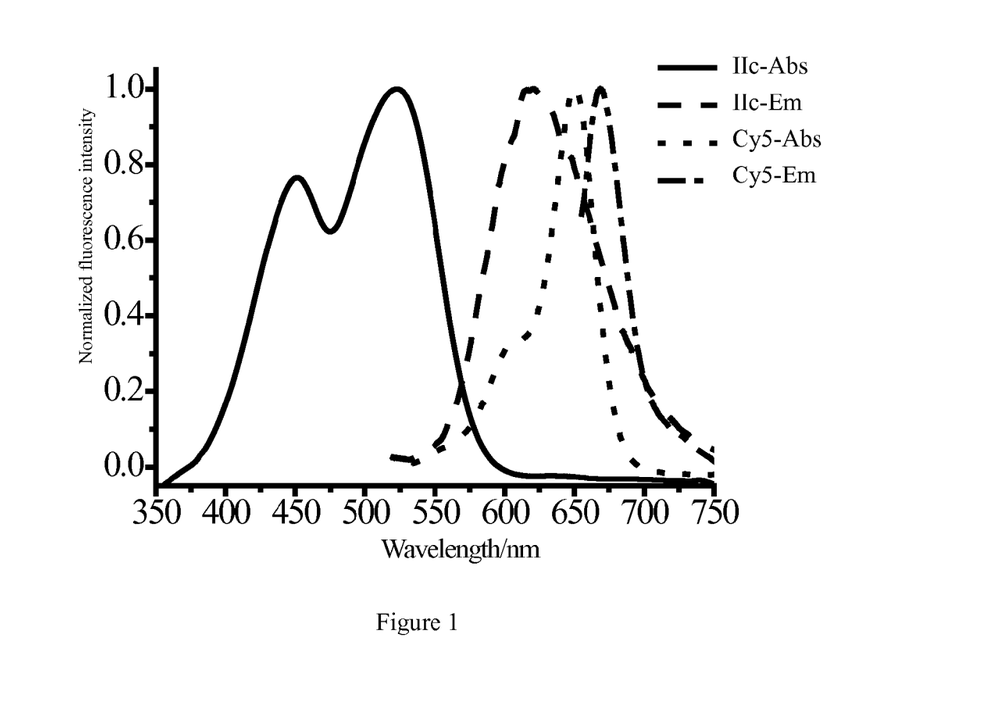
FIG. 1. Comparison of absorption and emission spectra of dye IIc with those of traditional Cy5 (solvent: ethanol, concentration: $1.0 \times 10^{-5}$ mol/L).

In the present invention, compounds IIa to IIg were synthesized based on compound II, and their spectral properties were investigated. The spectral properties of dyes in following examples were shown in table 1 and FIG. 1. Compared with the traditional pentamethine cyanine dye, for the novel pentamethine cyanine dye with N-substituting at β-position (deviated position), it was observed that, evident blue shift of absorption and emission wavelengths occurred, absorption wavelength blue shifted even largely than that of emission wavelength, absorption spectrum and fluorescence spectrum were no longer mirror-symmetric and had two absorption peaks and a single emission peak, and larger Stokes shift (minimum 60 and 150 nm, and maximum 90 and 230 nm) appeared. In addition, molar extinction coefficient of the dye was decreased and fluorescence quantum yield of the dye was also reduced, compared with those of the traditional pentamethine cyanine dye.

3. Noncovalent Interaction between Dye and Bio-Substrate

The novel cyanine dye has small fluorescence quantum yield, and the fluorescence quantum yield of dyes IIa, IIb and IIc in water are merely 0.002, 0.002 and 0.001, respectively, resulting in very low background fluorescence, which is advantageous for their bioapplication. In the present invention, the interaction between dyes (IIa, IIb and IIc) and bio-substrate (DNA and protein) was detected, and the results indicated that the fluorescence intensity of dyes could be largely increased by interaction with protein, but little fluorescence increase had been observed by interaction with ct-DNA.

3.1 Interaction between Dyes (IIa to IIc) and Bioactive Bovine Serum Albumin (BSA)

Figure 2:
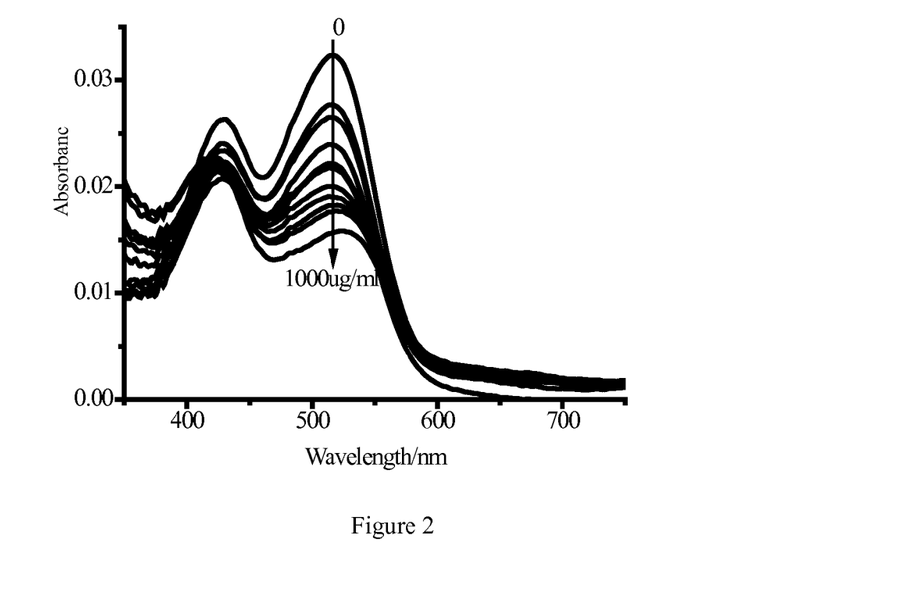
FIG. 2. Ultraviolet absorption spectra change titration of Cy5 with hydroxyethyl amino group-substituting at β-position (deviated position) (IIb: $1.0 \times 10^{-6}$ M) in PBS (pH=7.4) interacted with bovine serum albumin (BSA); excitation wavelength: 520 nm.
Figure 3:
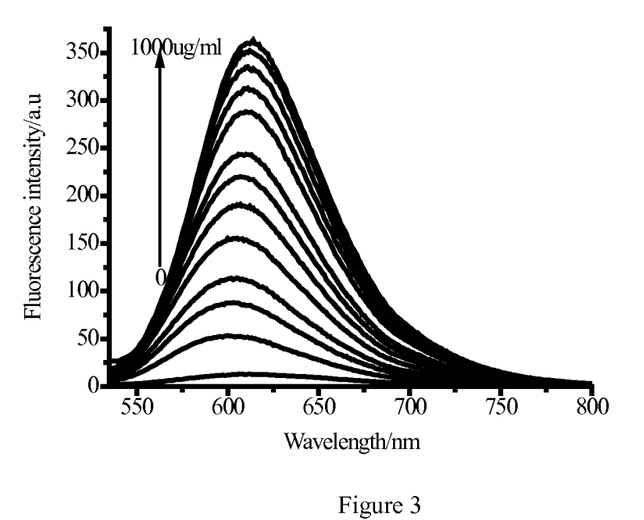
FIG. 3. Fluorescence emission spectra of Cy5 with hydroxyethyl amino group-substituting at β-position (deviated position) (IIb: $1.0 \times 10^{-6}$ M) in PBS (pH=7.4) interacted with bovine serum albumin (BSA); excitation wavelength: 520 nm.

BSA was employed to titrate the dye, and the results demonstrated that the fluorescence intensity of the dye solution (1 μM) was largely enhanced and UV absorbance of the dye was gradually decreased with addition of BSA, indicating that the dye interacted with BSA molecule and absorbed on BSA molecule. Especially for dyes IIb and IIc, the fluorescence intensity thereof was increased linearly with addition of BSA to arrive at more than 30 folds. The interaction results between dye IIb and BSA were shown in FIGS. 2 and 3. The interaction results of IIa and IIc with BSA were similar to those of IIb.

3.2 Dyes IIa to IIc Post-Stained Denatured BSA and Chymotrypsinogen A, Respectively.

BSA and chymotrypsinogen A were boiled for denaturation in water containing SDS and thioethanol for 10 minutes. After the denatured proteins were run by SDS-PAGE electrophoresis, the gel was immersed in the aqueous dye solution ($1.0 \times 10^{-4}$ M) for 2 hours to stain, washed with deion water for 2 hours and then imaged. The detection limits for the dye to post-stain protein on the gel were 20 ng for BSA and 50 ng for chymotrypsinogen A. (Yoshio Suzuki and Kenji Yokoyama, J. AM CHEM. SOC. 2005, 127, 17799-17802)

3.3 Interaction of Dyes IIa to IIc with Calf Thymus DNA

Figure 4:
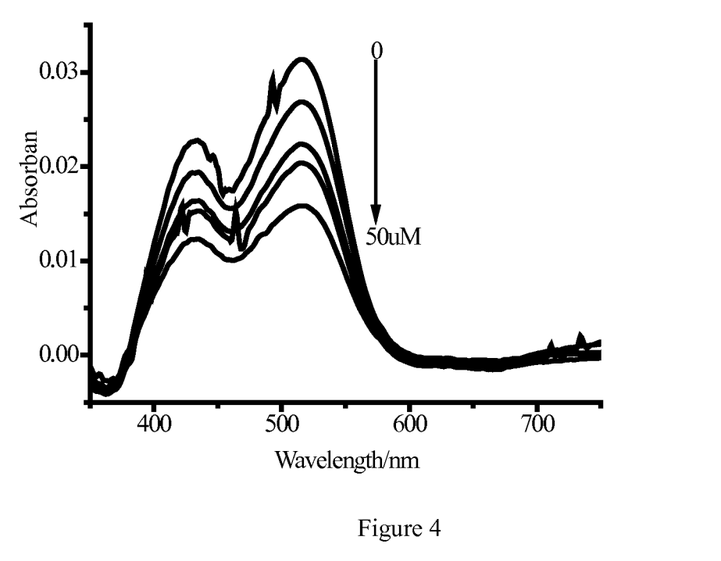
FIG. 4. Ultraviolet absorption spectra change titration of Cy5 with hydroxyethyl amino group-substituting at β-position (deviated position) (IIb: $1.0 \times 10^{-6}$ M) in PBS (pH=7.4) interacted with calf thymus DNA (ct-DNA); excitation wavelength: 520 nm.
Figure 5:
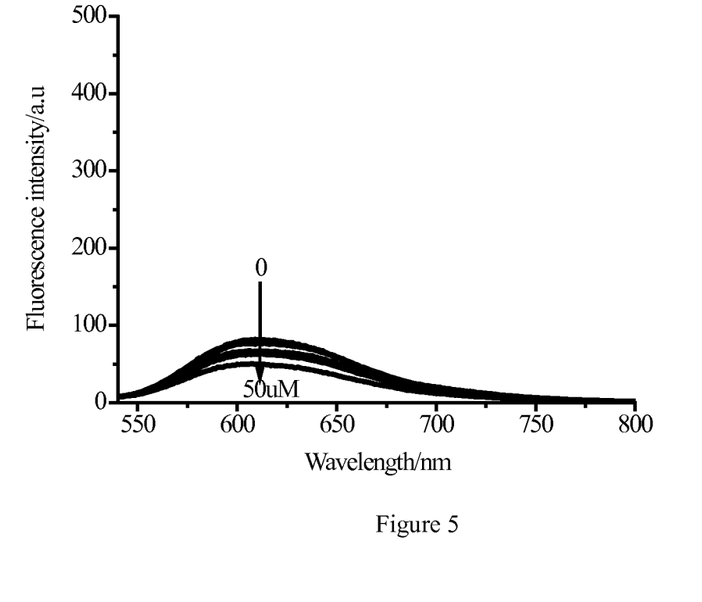
FIG. 5. Fluorescence emission spectra change titration of Cy5 with hydroxyethyl amino group-substituting at β-position (deviated position) (IIb: $1.0 \times 10^{-6}$ M) in PBS (pH=7.4) interacted with calf thymus DNA (ct-DNA); excitation wavelength: 520 nm.

From the interaction results of three dyes with calf thymus DNA, it can be known that no evident fluorescence increase was found after the interaction of the dye with the DNA. FIGS. 4 and 5 were titration figures of the interaction of dye IIb with calf thymus DNA. In addition, the decrease in UV absorption of the dye also indicated that the dye interacted with DNA but the interaction was different from that with BSA because the fluorescence intensity thereof was not increased. The interaction results of IIa and IIc with DNA were similar to that of IIb. All of these indicated DNA could be differentiated from protein by dyes IIa, IIb and IIc.

3.4 Fluorescence Imaging of Dye IIc and Traditional Cy5 in Live MCF-7 Cells

The dyes were cell membrane-permeable and could enter into live cells, demonstrating potential application of the dyes in the aspect of imaging in live cells. After the dyes entered into live cells, the fluorescence intensity was increased in a different level for protein and DNA. The dyes performed different selectivity between protein and DNA, which is very meaningful to investigate intracellular compositions in live cells.

The invention claimed is:

1. A pentamethine cyanine dye having a general formula (I) as follows:

wherein
X is the general formula of ($R_5$, $R_6$) amino group (II);
$R_1$ and $R_2$ are selected from the group consisting of $(CH_2)_n R_8$, $(CH_2)_m OR_9$, $(CHR_{10}CH_2O)_p R_9$ and $CH_2C_6H_4R_8$;
$R_3$, $R_4$ and $R_8$ are selected from the group consisting of H, $SO_3R_{11}$ and $CO_2R_{12}$;
$R_5$ is selected from the group consisting of $(CH_2)_n R_8$, $(CH_2)_m OR_9$ and $(CHR_{10}CH_2O)_p R_9$;
$R_6$ is selected from the group consisting of $(CH_2)_n R_8$, $(CH_2)_m OR_9$, $(CHR_{10}CH_2O)_p R_9$, m-$C_6H_4R_{17}$ and p-$C_6H_4R_{17}$;
$R_9$ selected from H or $C_{1-18}$ alkyls;
$R_{10}$ is H or $CH_3$;
$R_{11}$ is H or M;
M is selected from the group consisting of Na, K and N($R_{13}R_{14}R_{15}R_{16}$);
$R_{12}$ is selected from the group consisting of H, M, $R_7$ and $C_{1-18}$ alkyls;
$R_{13}$, $R_{14}$, $R_{15}$ and $R_{16}$ are selected from the group consisting of H, $C_{1-18}$ alkyls, $(CH_2)_m OR_9$ and $(CHR_{10}CH_2O)_p R_9$;
$R_{17}$ is selected from the group consisting of H, $NH_2$, $NHCOR_9$ and $(CH_2)_n R_8$;
n is an integer chosen from 0 and 2 to 18; and
m and p are integers independently chosen from 0 to 18.

2. A method for imaging a living cell, comprising the step of interacting a pentamethine cyanine dye of claim 1 with a living cell; and observing said living cell using an instrument.

3. The method of claim 2, wherein the instrument is a confocal laser scanning microscope.

4. A method for staining a bio-substrate, comprising the step of interacting a pentamethine cyanine dye of claim 1 with the bio-substrate.

5. The method of claim 4, wherein the bio-substrate is a DNA, a protein, or a liposome.

* * * * *